(12) United States Patent
Fotheringham et al.

(10) Patent No.: US 8,076,106 B2
(45) Date of Patent: Dec. 13, 2011

(54) METHOD TO INCREASE THE YIELD AND IMPROVE PURIFICATION OF PRODUCTS FROM TRANSAMINASE REACTIONS

(75) Inventors: Ian Fotheringham, Edinburgh (GB); Nicholas Oswald, Edinburgh (GB)

(73) Assignee: Richmond Chemical Corporation, Oakbrook Terrace, IL (US)

( * ) Notice: Subject to any disclaimer, the term of this patent is extended or adjusted under 35 U.S.C. 154(b) by 307 days.

(21) Appl. No.: 12/462,621

(22) Filed: Aug. 6, 2009

(65) Prior Publication Data

US 2009/0298134 A1    Dec. 3, 2009

Related U.S. Application Data

(62) Division of application No. 12/074,026, filed on Feb. 29, 2008, now Pat. No. 7,588,923.

(60) Provisional application No. 60/904,546, filed on Mar. 2, 2007, provisional application No. 60/926,482, filed on Apr. 27, 2007.

(51) Int. Cl.
  *C12P 7/04* (2006.01)
  *C12P 7/08* (2006.01)
  *C12P 7/12* (2006.01)
  *C12P 13/00* (2006.01)
  *C12P 7/40* (2006.01)

(52) U.S. Cl. ........ 435/106; 435/107; 435/108; 435/109; 435/110; 435/111; 435/112; 435/113; 435/114; 435/115; 435/116; 435/128; 435/136; 435/143

(58) Field of Classification Search .......... 435/106–116, 435/128, 136, 143
See application file for complete search history.

(56) References Cited

U.S. PATENT DOCUMENTS

| | | | |
|---|---|---|---|
| 4,518,692 A * | 5/1985 | Rozzell ................. | 435/116 |
| 4,600,692 A * | 7/1986 | Wood et al. ........... | 435/108 |
| 4,826,766 A * | 5/1989 | Rozzell ................. | 435/106 |
| 5,316,943 A * | 5/1994 | Kidman et al. ........ | 435/280 |
| 5,688,672 A * | 11/1997 | Kretzschmar et al. .. | 435/106 |
| 6,197,558 B1 * | 3/2001 | Fotheringham ........ | 435/106 |
| 6,365,380 B2 * | 4/2002 | Liu et al. .............. | 435/106 |
| 7,588,923 B2 * | 9/2009 | Fotheringham et al. .. | 435/106 |
| 2003/0032149 A1 * | 2/2003 | Lalonde ................. | 435/106 |

* cited by examiner

*Primary Examiner* — Herbert J. Lilling
(74) *Attorney, Agent, or Firm* — Avani C. Macaluso

(57) ABSTRACT

A process for producing high yields of enantioselective amino acids and chiral amines by reacting a keto acid or ketone and an amino acid donor in the presence of a transaminase biocatalyst to produce a keto acid by-product and an amino acid or amine product. Further reacting the keto acid by-product with a peroxide to increase the yield of additional amino acid or amine product.

14 Claims, 4 Drawing Sheets

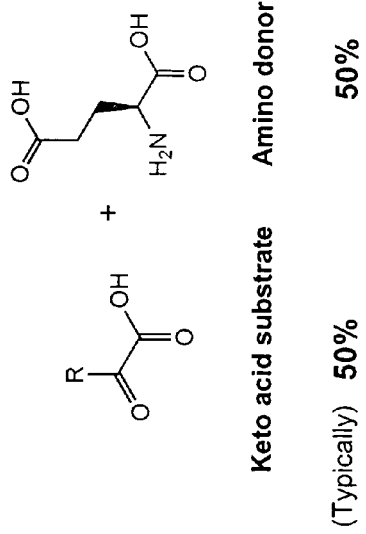
Figure 1A: Amino acid transaminase reaction substrates
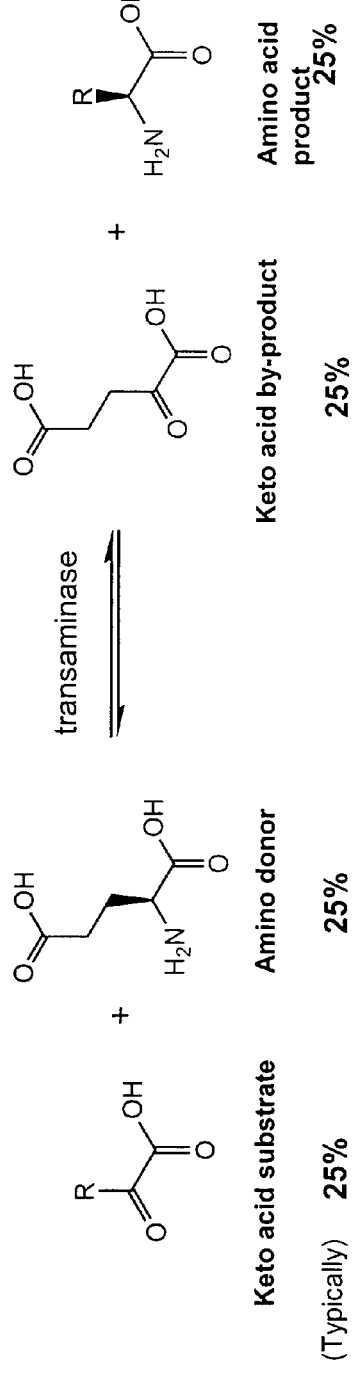
Figure 1B: Amino acid transaminase reaction substrates and products

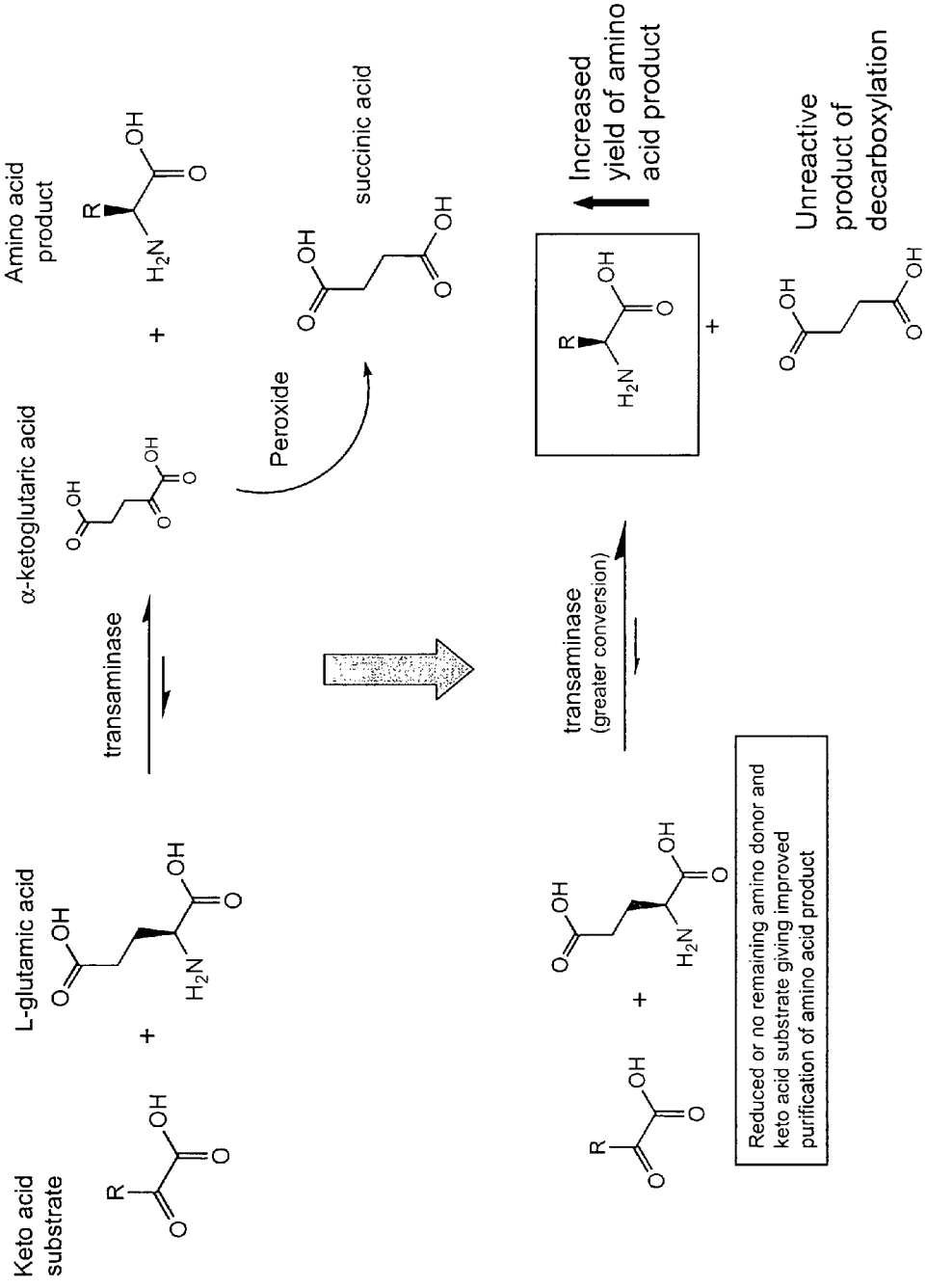
Figure 2A: Removal of keto acid by-product by peroxide to yield succinic acid which does not react with transaminases
Figure 2B: Removal of keto acid by-product by peroxide displaces equilibrium and increases yield of amino acid product

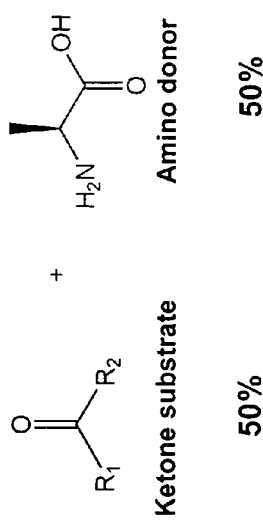
Figure 3A: Amine transaminase reaction substrates
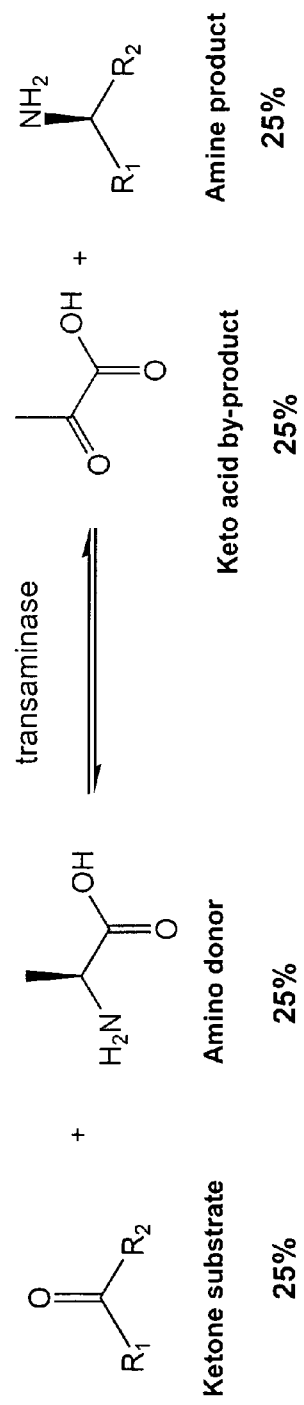
Figure 3B: Amine transaminase reaction substrates and products

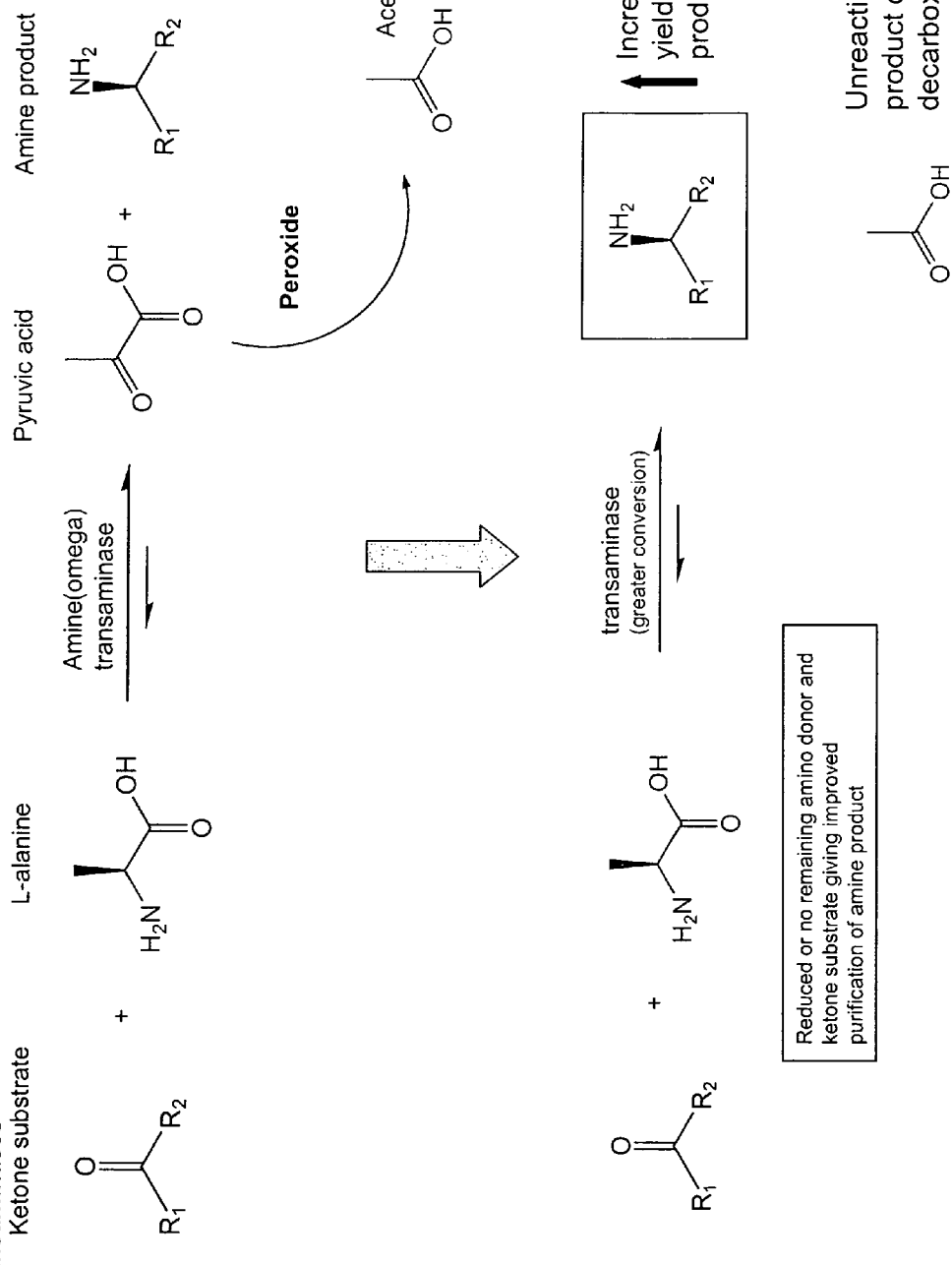
Figure 4A: Removal of keto acid by-product by peroxide to yield acetic acid which does not react with amine transaminases
Figure 4B: Removal of keto acid by-product by peroxide displaces equilibrium and increases yield of amine product

US 8,076,106 B2

METHOD TO INCREASE THE YIELD AND IMPROVE PURIFICATION OF PRODUCTS FROM TRANSAMINASE REACTIONS

CROSS-REFERENCE TO RELATED APPLICATIONS

This application is a divisional of application Ser. No. 12/074,026 filed Feb. 29, 2008 now U.S. Pat. No. 7,588,923, which is hereby incorporated by reference and upon which a claim of priority is based. This application also claims priority to U.S. Provisional Patent Application Ser. No. 60/904,546 filed Mar. 2, 2007 and U.S. Provisional Patent Application Ser. No. 60/926,482 filed Apr. 27, 2007, the entire disclosures of which are incorporated herein by reference. Priority to this application is claimed under 35 U.S.C. §§119, 120 and/or 121.

BACKGROUND OF THE INVENTION

1. Field of the Invention

The present invention is generally related to the enantioselective production of amino acids and chiral amines using transaminase biocatalysts. More particularly, the present invention relates to the use of peroxides to increase the yield and improve purification of non-naturally occurring amino acids and chiral amines.

2. Description of the Prior Art

Amino acids, including those not found in nature, are of increasing industrial importance because of their applications as intermediates in the pharmaceutical and agrochemical industries. Chiral amines and non-naturally occurring amino acids are two of the most valuable and rapidly growing classes of chemical compounds used in pharmaceutical, chemical and agrochemical discovery and development. The high value of these compounds is partly due to the difficulty of manufacturing them on a large scale. Part of this difficulty arises because many valuable amino acids and amines exist in two distinct 3-dimensional forms in a mixture that is difficult to separate, and usually only one form is required for a particular application. Generally, but with the exception of glycine, each of the common proteinogenic amino acids has a chiral, or asymmetric, α-carbon since there are four different functional groups bonded to the α-carbon. Thus, amino acids can exist as stereoisomers, which are compounds with the same molecular formula that differ in arrangement or configuration of their atoms in space. Enantiomers are stereoisomers, which are non-superimposable mirror images, and can exist for each chiral amino acid. The mirror image pairs of amino acids are designated D, dextrorotary, or L, levorotary, depending on whether the α-carbon of the amino acid corresponds to the D- or L-enantiomer of glyceraldehyde, the common reference compound. Most naturally occurring amino acids are of the L-configuration, although a number of D-amino acids occur in nature. Similarly the enantiomers of a given chiral amine are designated S- or R-according to their particular properties of optical rotation.

Chirality is critical to the function of compounds. In many pharmaceutical applications, the FDA has mandated that only one enantiomer of a compound may be used in a particular drug, and the opposite enantiomer may not be present at all. Thus, chemical and physical methods have been sought to prepare or separate the individual enantiomers of an amino acid or amine. To meet the industrial demand for these compounds, many methods have been described and developed to prepare enantiomerically pure amino acids and amines. These methods include the physical separation or resolution of enantiomeric pairs using chromatographic or crystallization methods, biocatalytic resolution of enantiomers using enzymes, asymmetric synthesis of single enantiomers using chemo- or biological catalysts, and, particularly for natural amino acids, fermentation methods using engineered microbes. Although each of these approaches has noted advantages in specific instances, each has been limited by narrow applicability to a few specific amino acids or amines required by the industry, and many are inherently compromised by low efficiency and relatively low yields.

For example, fermentation methods are limited to the production of natural amino acids, whereas most of the amino acids required for pharmaceutical and agrochemical applications do not occur in nature and accordingly are not suited for the complex biochemical pathways that are used in fermentative methods of production. Another approach has been to chemically manufacture amino acids and amines as racemic mixtures containing both D- and L-forms, and subsequently removing or destroying the undesired enantiomer by chemical or physical means in a process called resolution. Resolution methods are limited in almost all cases to a maximum single pass product yield of 50%, thereby incurring costs and generating waste in the form of solvents and unreacted by-products. Asymmetric synthesis of amino acids and amines using chemical and biological catalysts is often compromised by many factors including the narrow substrate ranges of the chemo- and biocatalysts used, inaccessible or expensive starting materials and stringent operating parameters for the catalysts including the need for organic solvents, chemo-catalysts, or complex methods to contain and regenerate cofactors required for the biocatalysts. As a result of these limitations, more general and robust processes have been sought for the commercial preparation of amino acids and chiral amines.

One biocatalytic method that has proven both robust and general to prepare D- and L-amino acids (both natural and unnatural) with greater than 99.9% enantiomeric purity employs microbial amino acid transaminase biocatalysts. Transaminases are well known in the art and have many properties desirable in an industrial biocatalyst. They often accept a broad range of substrates (starting materials), can be isolated widely from microbial sources, are stable, easily produced in recombinant systems, highly active and readily scaled up using low cost fermentation protocols. Amino acid transaminases exist in two stereoselective classes, either as L-selective or D-selective biocatalysts and so by choosing the appropriate transaminase an L- or D-amino acid can be made with high enantiomeric purity. Transaminases catalyze the reversible interconversion of amino acids and keto acids. The reversibility of this reaction is highly relevant to the present invention.

A general transaminase reaction is shown in FIG. 1A. In this reaction, a keto acid, which is the precursor of the desired amino acid product, is reacted with an amino acid called the amino donor. The transaminase enzyme exchanges the amino group of the amino donor with the keto group of the keto acid. The reaction therefore results in a new pair of amino and keto acids; the desired amino acid product and a new keto acid which is a by-product.

Transaminases, especially those from microbial sources, have been described in industrial applications to prepare unnatural amino acids. These transaminases include aromatic, aspartate and branched chain transaminases of *Escherichia coli*. Transaminase enzymes are ubiquitous throughout nature and many have been described in microbes. However, one of the main drawbacks to the efficiency and cost-competitiveness of transaminase based industrial bioprocesses is the equilibrium of this reaction, which typically provides close to a 1:1 ratio of substrates and products, wherein the "reverse" reaction occurs at the same rate as the forward reaction. Therefore, if at the start of the reaction, the composition of the starting material comprises 50% keto acid substrate and 50% amino donor, as shown in FIG. 1A, then at the end of the reaction the composition of the mixture will typically comprise 25% keto acid substrate and 25% amino donor and additionally 25% amino acid product and 25% keto acid by-product, as shown in FIG. 1B. The yield of the desired amino acid from its keto acid is therefore only 50% and the final product is only 25% of a mixture of four different chemicals. This means that 50% of the keto acid substrate is unreacted and wasted, and the isolation and purification of the desired amino acid product is severely compromised by the presence of a large number of unwanted chemicals.

Therefore, methods have been sought to influence the reaction yield by displacing the normal reaction equilibrium. Reducing or eliminating the keto acid by-product during the reaction can achieve this. Such removal in situ has the effect of reducing the rate of the reverse reaction such that the forward reaction dominates so that more substrate is then converted to product. In principle, if all the keto acid by-product can be removed then the reverse reaction can no longer occur and the forward reaction can proceed towards a theoretical 100% yield of the desired amino acid product. An additional benefit to the high yield of product would be that the amino acid donor would be completely consumed in the reaction, such that the only amino acid present in the final mixture is the desired product. In such a case, the isolation and purification of the amino acid product would be greatly simplified and improved.

Methods have been described to eliminate the keto acid by-product from the transaminase reaction, however all of these methods require that i) additional biocatalysts be added to the reaction; and/or ii) the amino acid donor used is aspartic acid. The additional enzymes that must be added increase the process cost and complexity, and also require to be produced by fermentation. Such processes lead to the generation of further by-products in the reaction. The limitation to having to use aspartic acid is due to the fact that the keto acid which derives from aspartic acid, oxaloacetic acid, can be readily decomposed, for example by additional enzymes and removed from the reaction, unlike many other keto acids. However, aspartic acid is not an ideal amino acid donor for this process, as most transaminase enzymes do not react with it and it can also lead to the production of further by-products such as the amino acid L-alanine.

The present invention provides a method to completely remove keto acid by-products from a transaminase reaction using peroxides thereby increasing the yield and purification of the desired amino acid product. Furthermore, the present invention is cost effective, does not require additional biocatalysts and is not limited to the use of aspartic acid as the amino donor.

SUMMARY OF THE INVENTION

The present invention is directed to the use of peroxides to eliminate the keto acid by-product from a transaminase catalyzed biotransformation. Peroxides efficiently effect the decarboxylation of keto acids, such as alphaketoglutaric acid, oxaloacetic acid or pyruvic acid, which derive from the amino acid donors glutamate, aspartate and alanine respectively. Most significantly, peroxides do not efficiently decarboxylate more sterically hindered keto acids that serve as precursors for the products of aminotransferase reactions, such as 3-methyl-2-oxo-pentanoic acid, 4-methyl-2-oxo-pentanoic acid, trimethylpyruvic acid, and ketopenicillamine, which are respectively the precursors of isoleucine, leucine, tert-leucine, and penicillamine.

A first aspect of the present invention is to increase the yield of amino acids and amines by reacting a ketone and/or a keto acid substrate in the presence of a transaminase biocatalyst and peroxide to produce a keto acid by-product and an amino acid and/or amine product. The process of the present invention can be applied to increase the enantioselective production of D-amino acids, L-amino acids, and/or chiral amines.

A second aspect of the present invention is to react a keto acid substrate with an amino acid donor in the presence of a transaminase biocatalyst and a peroxide to produce a first reaction mixture. The first reaction mixture contains a keto acid by-product and a first quantity of amino acid product. The addition of peroxide drives decarboxylation of the keto acid by-product. Consequently, decarboxylation of the keto acid by-product increases the yield of the amino acid product, when compared to the same process without using a peroxide, by reversing the rate of the reaction.

Another aspect of the present invention is to simultaneously add a peroxide to the transaminase reaction in such a way as to bring about decarboxylation of the keto acid by-product, but with no significant decarboxylation or reaction with any other compound in the mixture. In a preferred embodiment of the present invention, hydrogen peroxide is used, however other peroxides are suitable for decarboxylation such as, but not limited to, peroxyacids (peracids) such as peracetic acid ($CH_3CO_3H$), trifluoroperacetic acid and meta-chloroperoxybenzoic acid (MCPBA, 3-Cl—$C_6H_4CO_3H$), organic peroxides such as t-butyl peroxide ($(CH_3)_3COOH$), or other selective oxidants such as tetrapropylammonium perruthenate (TPAP), $MnO_2$, $KMnO_4$, ruthenium tetroxide and related compounds, osmium tetroxide and related compounds, chromate based oxidants, periodate, dioxirane, methyl trioxorhenium, hypochlorate, N-methylmorpholine N-oxide, ozone, iodosylbenzene, or o-iodoxybenzoic acid (IBX).

A further aspect of the invention is to add peroxide to the reaction mixture after the transaminase reaction has reached equilibrium and the transaminase biocatalyst has been removed. Following the reaction of peroxide with the keto acid by-product, the biocatalyst is returned to the reaction mixture and the reaction is allowed to proceed to a new equilibrium point. This cycle can be repeated until complete conversion of keto acid substrate to additional amino acid product has been achieved.

Another aspect of the present invention is increasing the yield of chiral amines in an amine transaminase reaction. The process requires reacting a ketone substrate and an amino acid donor with a transaminase biocatalyst and a peroxide to produce a keto acid by-product and a chiral amine product.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 1A is a schematic of general amino acid transaminase reaction substrates depicting substrate ratios;

FIG. 1B is a schematic of general amino acid transaminase reaction substrates and products depicting substrate and product ratios;

FIG. 2A is a schematic of the removal of keto acid by-product by peroxide to yield succinic acid which does not react with transaminases;

FIG. 2B is a schematic of the removal of keto acid by-product by peroxide causing equilibrium displacement to increase the yield and improve purification of a desired amino acid product;

FIG. 3A is a schematic of general amine transaminase reaction substrates depicting substrate ratios;

FIG. 3B is a schematic of general amine transaminase reaction substrates and products depicting substrate and product ratios;

FIG. 4A is a schematic of the removal of keto acid by-product by peroxide to yield acetic acid which does not react with transaminases; and FIG. 4B is a schematic of the removal of keto acid by-product by peroxide causing equilibrium displacement to increase the yield and improve purification of a desired amine product.

DETAILED DESCRIPTION

The present invention is capable of embodiments in many different forms. Preferred embodiments of the invention are disclosed with the understanding that the present disclosure is to be considered as exemplifications of the principles of the invention and are not intended to limit the broad aspects of the invention to the embodiments illustrated.

Amino acid transaminase biocatalysts with high enantioselectivity for either L- or D-amino acids can be isolated from natural sources, including but not limited to, microorganisms and are considered suitable for use in the present invention. Genes encoding transaminases are known in the art and can be identified using bioinformatic methods or biological screening methods, and isolated using methods such as polymerase chain reaction (PCR). Genes encoding transaminases may be introduced into recombinant microorganisms on plasmid vectors available from commercial sources and overproduced in recombinant cells using well-characterized, heterologous regulatory regions. Transaminase biocatalysts may be prepared by fermentation using recombinant microorganisms including, but not limited to, *Escherichia coli, Bacillus, Pseudomonas* and yeast such as *Saccharomyces* and *Pichia*. Transaminases can be prepared as wild type enzymes or as variants, generated by random or rational mutation of the genes encoding the enzymes. Transaminases are pyridoxal phosphate dependent enzymes that can be used in a variety of formulations, including whole cells, purified enzymes or partially purified cell fractions prepared by methods such as ammonium sulfate precipitation, immobilized whole cells, or enzymes on or within solid supports.

An example of a transaminase biocatalyst that can be used to produce enantioselective amino acid products is the branched chain transaminase of *E. coli* K12 named IlvE, encoded by the ilvE gene. The gene encoding the IlvE transaminase can be easily obtained by those skilled in the art, using PCR to amplify the gene from the chromosomal DNA of *E. coli*, based on information derived from bioinformatics and *E. coli* genome sequence available online. The ilvE gene can be inserted into one or more of numerous plasmid expression systems that are commercially available and the IlvE transaminase biocatalyst can then be produced at high levels in recombinant strains of *E. coli*. Similarly many other microbial transaminases, such as aromatic transaminases or omega (ω) transaminases can be isolated and produced in recombinant strains using standard cloning methods and publicly available genetic information.

It has been discovered that one of the major limitations of using transaminases lies in the reaction equilibrium that typically leads to the desired amino acid product representing only 25% of the chemical compounds in the mixture at the end of the reaction. Thus, the present invention utilizes methods of reaction equilibrium displacement to alter the end point of the reaction such that a higher yield of amino acid product is obtained.

Referring now to the drawings in general, the illustrations are for the purpose of describing a preferred embodiment of the invention and are not intended to limit the invention thereto. The present invention can be used for the production of L-amino acids, such as but not limited to, L-isoleucine, L-leucine, L-tert-leucine, and L-penicillamine. In one embodiment of the present invention, a whole cell transaminase biocatalyst is combined with a keto acid substrate and an amino acid donor, as shown in FIGS. 1A and 1B. Almost all known microbial L-amino acid transaminases accept L-glutamic acid (unlike L-aspartic acid or other amino acids) as the amino acid donor. In one embodiment a keto acid substrate and an amino acid donor are reacted in the presence of a transaminase. The transaminase reaction is allowed to proceed to the equilibrium point, which can be determined by sampling techniques known in the art, at which point the biocatalyst is removed and the reaction mixture is treated with a peroxide in a quantity at least about equimolar to the concentration of alphaketoglutarate present. In one embodiment it is preferred to treat the mixture in excess of the amount equimolar to the concentration of the keto acid by-product in order to compensate for any peroxide that may be consumed by the biocatalyst or react with the keto acid donor. To ensure the concentration of the peroxide is not compromised, it is recommended in one embodiment to remove the biocatalyst when treating the amino acid transaminase reaction with peroxide.

Referring to FIGS. 2A and 2B, the peroxide is added when the reaction reaches a point of equilibrium in which the forward and reverse rates are equal. After the addition of peroxide and decarboxylation of the keto acid by-product, the reverse reaction is slowed because the keto acid by-product is present is a reduced amount. As shown in FIGS. 2A and 2B, the product of decarboxylation, succinate, cannot be transaminated by the biocatalyst because it has no keto group. As a result the forward reaction rate is faster and therefore more amino acid product is formed. Although more keto acid by-product is also formed, it continues to be decomposed by the peroxide so the reaction is generally pushed to the right.

FIGS. 2A and 2B illustrate L-glutamic acid as the amino donor and accordingly alphaketoglutarate as the keto acid by-product which can be readily decarboxylated with a peroxide. Similarly, if L-alanine is utilized as the amino acid donor, then the resulting keto acid by-product will be pyruvic acid that decarboxylates to acetate. Upon decarboxylation of the pyruvic acid, the rate of the reverse reaction is reduced because acetate cannot be transaminated.

After a period of reaction the biocatalyst is returned to the mixture and the reaction allowed to proceed for a further period until a new equilibrium is reached that yields an increased amount of amino acid product, or additional amino acid product as shown in FIGS. 2A and 2B. This process can be repeated until complete conversion of the keto acid substrate to additional amino acid product has been achieved. In one embodiment of the present invention, a whole cell transaminase biocatalyst is combined with a keto acid substrate and one of the amino acid donors such as, but not limited to, L-glutamic acid, L-aspartic acid or L-alanine. It is preferred that the amino acid donors are selected so that the keto acid by-product which they produce are more susceptible to decarboxylation than the substrate keto acid, such as but not limited to alphaketoglutaric acid, oxaloacetatic acid, or pyruvic acid which are derived from the amino acid donors glutamic acid, aspartic acid, and alanine respectively. The present invention further contemplates use with keto acid substrates that are more sterically hindered than the keto acid by-product of the amino acid donor, such as but not limited to 3-methyl-2-oxo-pentanoic acid, 4-methyl-2-oxo-pentanoic acid, trimethylpyruvic acid, or ketopenicillamine which are respectively precursors of isoleucine, leucine, tert-leucine, and penicillamine. Significantly, peroxides do not efficiently decarboxylate sterically hindered keto acid substrates. The process of the present invention can be applied to the production of enantioselective L-amino acids, such as but not limited to L-isoleucine, L-tert-leucine, L-leucine, and L-penicillamine using an L-amino acid transaminase. The L-amino acid donors generate keto acid by-products, therefore the addition of peroxide activates decarboxylation of the keto acid by-products to further increase the yield of L-amino acid products.

In a preferred embodiment of the present invention hydrogen peroxide is used to decarboxylate the keto acid by-product and thereby displacing the normal equilibrium. Other possible peroxides suitable for decarboxylation include, but are not limited to, peroxyacids (peracids) such as peracetic acid ($CH_3CO_3H$), trifluoroperacetic acid and meta-chloroperoxybenzoic acid (MCPBA, 3-Cl—$C_6H_4CO_3H$), organic peroxides such as t-butyl peroxide (($CH_3)_3COOH$), or other selective oxidants such as tetrapropylammonium perruthenate (TPAP), manganese oxide ($MnO_2$), potassium permanganate ($KMnO_4$), ruthenium tetroxide and related compounds, osmium tetroxide and related compounds, chromate based oxidants, periodate, dioxirane, methyl trioxorhenium, hypochlorate, N-methylmorpholine N-oxide, ozone, iodosylbenzene, or o-iodoxybenzoic acid (IBX). It is also possible to use reagents that produce peroxides or appropriate oxidants in situ.

The process of the present invention can also be applied in the same way to the production of D-amino acids, such as, but not limited to, D-isoleucine, D-phenylalanine, D-tert-leucine, D-penicillamine and D-tyrosine, using a D-amino acid transaminase instead of an L-amino acid transaminase and using a D-amino acid as the amino acid donor instead of an L-amino acid. For example, D-amino acid amino donors such as, but not limited to, D-glutamic acid, D-aspartic acid, and D-alanine may be used. All other aspects of the reaction are substantially consistent to that for the L-amino acid transaminase as described above. D-amino acid transaminases, such as that from *Bacillus sphaericus* have been described extensively in the scientific literature and the genes which encode these biocatalysts can be readily isolated, cloned and expressed in recombinant microbial hosts, such as *E. coli*, using methods well known in the art. The D-amino acid amino donors generate the same keto acid by-products as their corresponding L-amino acid amino donor counterparts. Therefore, the process benefits from peroxide decarboxylation of keto acid by-products which are obtained using L-amino acid amino donors, and are equally applicable in the case of D-amino acid amino donors used with D-amino acid transaminases to yield D-amino acid products.

In another embodiment of the present invention, the transaminase biocatalyst is compartmentalized within the lumen of a membrane such as a hollow fiber membrane, or a membrane bioreactor, having a pore size that does not permit the biocatalyst to enter the permeate, but through which molecules of substrate and product can pass freely. The permeate stream is treated with hydrogen peroxide and returned to the lumen to react further. If desired any residual peroxide can be completely decomposed using a catalase enzyme prior to returning the permeate stream to the lumen. In this way a semi-continuous or continuous process is operated whereby the keto acid by-product reacts with the peroxide, but the peroxide does not come into contact with the biocatalyst. Thus, there is no wastage of peroxide by reaction with the biocatalyst or any reduction in performance of the biocatalyst by reaction with the peroxide.

In another embodiment of the present invention, the transaminase biocatalyst is prepared in a recombinant fermentation of *E. coli* using standard fed-batch fermentation protocols known in the art to achieve a high biomass. The cells are then used in a bioreaction as a whole cell biocatalyst with a keto acid precursor of a desired amino acid product and an amino donor comprising, but not limited to, L-glutamic acid, L-aspartic acid or L-alanine.

In a further embodiment of the present invention, the transaminase biocatalyst is prepared in a recombinant fermentation of *E. coli* using standard fed-batch fermentation protocols known in the art to achieve a high biomass. The cells are broken using mechanical means and the transaminase is recovered as an enriched, highly active and highly stable ammonium sulfate fraction. The fraction is then used with a keto acid precursor of a desired amino acid product and an amino acid donor comprising, but not limited to L-glutamic acid, L-aspartic acid or L-alanine or the corresponding D-amino acids for a D-amino acid transaminase.

In a further embodiment of the present invention, ω-amino acid transaminases are used to produce chiral amines, as shown in FIGS. 3A and 3B. ω-Amino acid transaminases, such as those from *Bacillus thuringiensis, Alcaligenes denitrificans* and *Vibrio fluvialis* have been described extensively in the scientific literature and the genes which encode these biocatalysts can be readily isolated, cloned and expressed in recombinant microbial hosts, such as *E. coli*, using methods well known in the art. The ω-amine transaminases typically use L-alanine as the amino donor instead of L-glutamic acid. The resulting keto acid by-product is therefore pyruvic acid, which is readily decarboxylated by peroxide, as shown in Table 1. In a preferred embodiment the peroxide used for decarboxylation of pyruvic acid is hydrogen peroxide. All other aspects of the reaction are similar to that for the L-amino acid transaminase as described above.

Consequently the process benefits from peroxide decarboxylation of keto acid by-products, which are obtained using L-amino acid amino donors with L-amino acid transaminases, or D-amino acid amino donors with D-amino acid transaminases, are equally applicable in the case of ω-amino acid transaminases since the amino donor is also an L-amino acid such as L-alanine. For the production of chiral amines, L-alanine can be used with a ketone substrate to produce a chiral amine and pyruvic acid as the keto acid by-product, as illustrated in FIGS. 4A and 4B. By selecting a ω-amino acid transaminase with the appropriate selectivity for either S- or R-amine synthesis, this process can be used to prepare either S- or R-chiral amines. In either case L-alanine will serve as the amino donor. A further advantage of the present invention in utilizing amine transamination for the production of chiral amines is that the substrate for the desired amine product is not a keto acid but rather a ketone, which does not possess a carboxyl group and is therefore not subject to potential decarboxylation by peroxide. Thus, only the keto acid present in this reaction, and is therefore capable of being decarboxylated, is pyruvic acid, which is generated from L-alanine the amino acid donor. This will potentially broaden the applicability of the present invention to include any chiral amine that can be produced by an ω-amino acid transaminase. There is no requirement that the keto substrate be resistant to decarboxylation by peroxide since the substrate is a ketone, and not a keto acid, and thus contains no carboxyl group.

Transamination of the substrates is carried out in water in a bioreactor using an aliquot of the enzyme with the substrate typically at a concentration of 50 mM to 2 M. The reaction parameters such as pH, temperature, and mixing are maintained at levels that favor optimal biocatalytic activity and stability. Conditions can be readily established to purify amino acid products from organic acids such as succinate or acetate because the latter are uncharged when the solution is brought to a low pH.

EXAMPLES

Example 1

Reaction of 3-Methyl-2-Oxopentanoate Precursor of Desired Amino Acid Product L-Isoleucine and Amino Donor L-Glutamic Acid A reaction mixture comprising 10 mls of water containing 100 mM 3-methyl-2-oxopentanoate and 100 mM L-glutamic acid at pH7.5 and 100 mg/ml whole cell biocatalyst RCI66 is incubated at 40° C. with agitation at 250 rpm for 7 hrs. The biocatalyst is then removed by centrifugation and the alpha-ketoglutarate content measured by HPLC. The reaction mixture is then cooled to 4° C. and a sub-equimolar concentration of hydrogen peroxide is added to the reaction mixture that is then incubated at 4° C. for 30 minutes. The original biocatalyst is then returned to the reaction which is returned to the 40° C. incubator and allowed to proceed for a further 2 hrs at which point the biocatalyst is removed as before and the reaction mixture treated with hydrogen peroxide as before. The original biocatalyst is discarded and fresh biocatalyst at 100 mg/ml is then added to the reaction which is allowed to proceed for a further 1.5 hrs to completion. A control reaction is setup that is identical in initial composition and is treated identically except that no hydrogen peroxide is added. Samples are taken for analysis throughout both reactions and analysed by HPLC to determine the concentration of amino acid substrate and product and keto acid substrate and product. The untreated control reaction showed a final conversion of 3-methyl-2-oxopentanoate substrate to L-isoleucine product of 44% whereas the hydrogen peroxide treated reaction reached a conversion of 60%.

Example 2

Reaction of Phenylpyruvic Acid Precursor of Desired Amino Acid Product D-Phenylalanine and Amino Donor D-Glutamic Acid A reaction mixture comprising 10 mls of water containing 100 mM phenylpyruvic acid and 100 mM D-glutamic acid at pH7.5 and 100 mg/ml whole cell biocatalyst RC255 is incubated at 40° C. with agitation at 250 rpm for 7 hrs. RC255 is a recombinant E. coli strain which contains a plasmid which expresses the cloned D-aminotransferase from Bacillus sphaericus under the control of the lambda CI857 promoter. The biocatalyst is then removed by centrifugation and the alphaketoglutarate content measured by HPLC. The reaction mixture is then cooled to 4° C. and a sub-equimolar concentration of hydrogen peroxide is added to the reaction mixture that is then incubated at 4° C. for 30 minutes. The original biocatalyst is then returned to the reaction which is returned to the 40° C. incubator and allowed to proceed for a further 2 hrs at which point the biocatalyst is removed as before and the reaction mixture treated with hydrogen peroxide as before. The original biocatalyst is discarded and fresh biocatalyst at 100 mg/ml is then added to the reaction which is allowed to proceed for a further 1.5 hrs to completion. A control reaction is setup that is identical in initial composition and is treated identically except that no hydrogen peroxide is added. Samples are taken for analysis throughout both reactions and analyzed by HPLC to determine the concentration of amino acid substrate and product and keto acid substrate and product. Based on the fact that the relative rate of decarboxylation of alpha-ketoglutarate by hydrogen peroxide is much greater than that of phenylpyruvic acid, the hydrogen peroxide treated reaction would be expected to proceed to a greater yield of D-phenylalanine than the control reaction.

Example 3

Reaction of 2-Butanone Precursor of Desired Amine Product S-2-Butylamine and Amino Donor L-Alanine A reaction mixture comprising 10 mls of water containing 2 mM 2-butanone and 20 mM L-alanine at pH 7.5 and 100 mg/ml whole cell biocatalyst RC209. RC209 is a recombinant strain of E. coli K12 which contains a plasmid which expresses the cloned omega transaminase of A. denitrificans under control of the lambda CI857 promoter region. The reaction is incubated at 37° C. with agitation at 250 rpm for 4 hrs. The biocatalyst is then removed by centrifugation and hydrogen peroxide is added to a final concentration of 10 mM. The original biocatalyst is then returned to the reaction which is returned to the 37° C. incubator and allowed to proceed for a further 2 hrs at which point the biocatalyst is removed as before and the reaction mixture treated with hydrogen peroxide as before. The original biocatalyst is discarded and fresh biocatalyst at 100 mg/ml is then added to the reaction which is allowed to proceed for a further 2 hrs to completion. A control reaction is setup that is identical in initial composition and is treated identically except that no hydrogen peroxide is added. Samples are taken for analysis throughout both reactions and analyzed by HPLC to determine the concentration of amino acid substrate and amine product and keto acid substrate and product. On the basis that pyruvic acid is efficiently decarboxylated by peroxide, this treatment would be expected to drive the reaction to an improved yield versus the control reaction.

Example 4

Reaction of 2-Butanone Precursor of Desired Amine Product S-2-Butylamine and Amino Donor L-Alanine A reaction mixture comprising 10 mls of water containing 2 mM 2-butanone and 2 mM L-alanine at pH 7.5 and 100 mg/ml whole cell equivalents of partially purified RC209 is incubated at 37° C. with agitation at 250 rpm for 8 hrs. During the reaction, hydrogen peroxide is continuously added at a rate of 20 μmol per hour. The reaction is then supplemented with a further 100 mg/ml whole cell equivalents of partially purified RC209. The reaction is allowed to proceed for a further 8 hours with hydrogen peroxide addition as before. A control reaction is setup that is identical in initial composition and is treated identically except that no hydrogen peroxide is added. Samples are taken for analysis throughout both reactions and analyzed by HPLC to determine the concentration of amino acid substrate and amine product and keto acid substrate and product. On the basis that pyruvic acid is efficiently decarboxylated by peroxide this treatment would be expected to drive the reaction to an improved yield versus the control reaction.

Example 5

Demonstration of Relative Rates of Decarboxylation of Keto Acids Alphaketoglutaric Acid and Pyruvic Acid Versus More Sterically Hindered Keto Acids Such as 3-Methyl-2-Oxopentanoate, 4-Methyl-2-Oxopentanoate, Phenylpyruvic Acid, and Trimethylpyruvic Acid Independent 10 mM solutions of each keto acid are prepared. A sample is taken from each and the initial absorbance at 210 nm of each solution is measured by HPLC to establish the absorbance value which corresponds to a 10 mM concentration. A 5-10 fold molar excess of hydrogen peroxide is then added to each solution and each is incubated at 4° C. and sampled for similar HPLC analysis over a period of 60 minutes. Decarboxylation of each keto acid by hydrogen peroxide over time is monitored by the reduction in the absorbance at 210 nm shown by the peak corresponding to each individual keto acid. The rates of decarboxylation of each keto acid are then calculated using standard methods and are shown in Table 1.

Table 1 shows the relative rates of decarboxylation of each keto acid, including the sterically hindered compounds, relative to alphaketoglutarate. Clear and very large differences are observed in the relative rates of decarboxylation that correspond to the relative steric hindrance of each compound towards the reaction with hydrogen peroxide.

TABLE 1

| Compound | Decarbox. rate (mM/min) | Relative rate to αKG |
| --- | --- | --- |
| alphaketoglutarate | 6.89 | 1.0000 |
| Pyruvic acid | 4.97 | 0.7222 |
| 3-methyl-2-oxopropanoate | 0.32 | 0.0459 |
| 4-methyl-2-oxopropanoate | 0.50 | 0.0719 |
| Trimethyl pyruvic acid | 0.03 | 0.0041 |
| Phenylpyruvic acid | 0.10 | 0.0149 |

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the following claims.

What is claimed is:

1. A process for increasing the yield of amines in a transaminase reaction, the process comprising:
 a) providing a ketone substrate;
 b) providing an amino acid donor; and
 c) reacting the ketone substrate and the amino acid donor in the presence of a transaminase biocatalyst and a peroxide to increase the yield of an amine product compared to the same process without using a peroxide.

2. A process for increasing the yield of amines in a transaminase reaction, the process comprising:
 a) providing a ketone substrate;
 b) providing an amino acid donor;
 c) reacting the ketone substrate and the amino acid donor in the presence of a transaminase biocatalyst and a peroxide to produce a reaction mixture having a keto acid by-product and an amine product, wherein the amine product yield is increased compared to the same process without using peroxide.

3. The process of claim 2, further comprising the step of allowing the reaction mixture to proceed to or approximately to a first equilibrium point.

4. The process of claim 3, further comprising temporarily removing the transaminase biocatalyst after the first equilibrium point is reached.

5. The process of claim 2, further comprising decarboxylating the keto-acid by-product with the peroxide.

6. The process of claim 2, wherein the transaminase biocatalyst is compartmentalized within a lumen of a membrane.

7. The process of claim 2, wherein the keto acid by-product reacts with the peroxide in a semi-continuous or continuous manner.

8. The process of claim 2, wherein the concentration of the peroxide is at least about equimolar to a concentration of the keto acid by-product.

9. The process of claim 2, wherein the amino acid donor comprises L-alanine.

10. The process of claim 2, wherein the keto acid by-product comprises pyruvic acid.

11. The process of claim 2, wherein the peroxide is an organic peroxide.

12. The process of claim 2, wherein the peroxide is a peroxyacid.

13. The process of claim 2, wherein the peroxide comprises hydrogen peroxide ($H_2O_2$), peracetic acid ($CH_3CO_3H$), trifluoroperacetic acid, meta-chloroperoxybenzoic acid (MCPBA, $3\text{-Cl---}C_6H_4CO_3H$), t-butyl peroxide ($(CH_3)_3COOH$), tetrapropylammonium perruthenate (TPAP), manganese oxide ($MnO_2$), potassium permanganate ($KMnO_4$), ruthenium tetroxide, osmium tetroxide, chromate based oxidants, periodate, dioxirane, methyl trioxorhenium, hypochlorate, N-methylmorpholine N-oxide, ozone, iodosylbenzene, and/or o-iodoxybenzoic acid (IBX).

14. A process for increasing the yield of amines in a transaminase reaction, the process comprising:
 a) providing a ketone substrate;
 b) providing an amino acid donor; and
 c) reacting the ketone and the amino acid donor in the presence of a transaminase biocatalyst and hydrogen peroxide to increase the yield of an amine product compared to the same process without using hydrogen peroxide.

* * * * *